(12) United States Patent
Surendranath et al.

(10) Patent No.: US 10,098,595 B2
(45) Date of Patent: Oct. 16, 2018

(54) LOW POWER PHOTON COUNTING SYSTEM

(71) Applicant: Texas Instruments Incorporated, Dallas, TX (US)

(72) Inventors: Nagesh Surendranath, Bangalore (IN); Rakul Viswanath, Chennai (IN); Sandeep Kesrimal Oswal, Bangalore (IN)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 203 days.

(21) Appl. No.: 14/871,245

(22) Filed: Sep. 30, 2015

(65) Prior Publication Data

US 2017/0035376 A1    Feb. 9, 2017

(30) Foreign Application Priority Data

Aug. 6, 2015  (IN) .......................... 4090/CHE/2015

(51) Int. Cl.
| | |
|---|---|
| *A61B 6/03* | (2006.01) |
| *G01T 1/17* | (2006.01) |
| *G01T 1/24* | (2006.01) |
| *A61B 6/00* | (2006.01) |

(52) U.S. Cl.
CPC .......... *A61B 6/4241* (2013.01); *A61B 6/4208* (2013.01); *A61B 6/4233* (2013.01); *G01T 1/171* (2013.01); *G01T 1/24* (2013.01); *A61B 6/032* (2013.01)

(58) Field of Classification Search
CPC ..... A61B 6/032; A61B 6/4208; A61B 6/4233; A61B 6/4241

USPC .............................. 378/19, 98.8; 250/370.09
See application file for complete search history.

(56) References Cited

U.S. PATENT DOCUMENTS

| | | | | |
|---|---|---|---|---|
| 4,070,578 | A * | 1/1978 | Timothy | G01T 1/2957 250/207 |
| 4,255,659 | A * | 3/1981 | Kaufman | A61B 6/032 250/370.09 |
| 4,595,909 | A | 6/1986 | Jarrett | |
| 4,647,903 | A | 3/1987 | Ryu | |
| 5,508,507 | A * | 4/1996 | Nelson | H04N 5/30 250/214 LA |
| 5,693,946 | A * | 12/1997 | Vickers | G01T 1/2928 250/370.08 |
| 5,943,388 | A * | 8/1999 | Tümer | G01V 5/0041 378/98.11 |
| 6,300,635 | B1 * | 10/2001 | Brambilla | G01T 1/026 250/336.1 |
| 6,324,244 | B1 * | 11/2001 | Lauter | H03M 1/186 378/19 |

(Continued)

*Primary Examiner* — Allen C. Ho
(74) *Attorney, Agent, or Firm* — John R. Pessetto; Charles A. Brill; Frank D. Cimino (57) ABSTRACT

The disclosure provides a circuit that includes a charge sensitive amplifier (CSA) that generates an integrated signal in response to a current signal. An active comparator is coupled to the CSA. The active comparator receives the integrated signal and a primary reference voltage signal, and generates an event detect signal. A first delay element is coupled to the active comparator and provides a fixed delay to the event detect signal to generate a convert signal. A discriminator system is coupled to the CSA. The discriminator system samples the integrated signal when activated by the convert signal.

20 Claims, 6 Drawing Sheets

(56) References Cited

U.S. PATENT DOCUMENTS

| | | | | |
|---|---|---|---|---|
| 6,678,039 B2* | 1/2004 | Charbon | G01S 7/487 | |
| | | | 342/135 | |
| 6,781,134 B1* | 8/2004 | Murray | G01T 7/00 | |
| | | | 250/370.12 | |
| 6,917,041 B2* | 7/2005 | Doty | H04N 5/37213 | |
| | | | 250/370.08 | |
| 6,998,913 B2* | 2/2006 | DeGeronimo | H03F 1/34 | |
| | | | 330/288 | |
| 7,065,175 B2* | 6/2006 | Green | G01N 23/20 | |
| | | | 378/57 | |
| 7,139,024 B2* | 11/2006 | Lu | H04N 3/155 | |
| | | | 348/303 | |
| 7,157,715 B1* | 1/2007 | Crain, Jr. | G01T 1/026 | |
| | | | 250/370.07 | |
| 7,157,716 B2* | 1/2007 | Kitaguchi | G01T 1/24 | |
| | | | 250/370.12 | |
| 7,170,049 B2* | 1/2007 | Iwanczyk | G01T 1/2928 | |
| | | | 250/208.1 | |
| 7,223,979 B1* | 5/2007 | Crain, Jr. | G01T 1/026 | |
| | | | 250/370.07 | |
| 7,250,896 B1 | 7/2007 | Hesener | | |
| 7,339,175 B1* | 3/2008 | Drummond | G01T 1/2928 | |
| | | | 250/370.01 | |
| 7,362,175 B2* | 4/2008 | Argues | H03F 1/0205 | |
| | | | 330/264 | |
| 7,368,722 B2* | 5/2008 | Berthold | G01T 1/20 | |
| | | | 250/362 | |
| 7,388,210 B2* | 6/2008 | Ouvrier-Buffet | G01T 1/17 | |
| | | | 250/370.13 | |
| 7,501,965 B2* | 3/2009 | Janakiraman | H03M 1/0809 | |
| | | | 341/118 | |
| 7,514,688 B2* | 4/2009 | Broennimann | H01L 27/14661 | |
| | | | 250/370.11 | |
| 7,528,375 B2* | 5/2009 | Matsumoto | G01T 1/2928 | |
| | | | 250/370.01 | |
| 7,582,878 B2* | 9/2009 | Shahar | G01T 1/2928 | |
| | | | 250/370.09 | |
| 7,592,603 B2* | 9/2009 | Hsi | G01T 1/02 | |
| | | | 250/361 R | |
| 7,615,753 B2* | 11/2009 | Audebert | G01T 1/17 | |
| | | | 250/370.07 | |
| 7,615,755 B2* | 11/2009 | Coello | H04N 3/155 | |
| | | | 250/370.01 | |
| 7,634,061 B1* | 12/2009 | Tümer | G01T 1/247 | |
| | | | 378/62 | |
| 7,738,631 B2* | 6/2010 | Rundle | G01N 21/49 | |
| | | | 250/370.09 | |
| 7,760,123 B2* | 7/2010 | Rao | G06G 7/18 | |
| | | | 341/155 | |
| 7,818,047 B2* | 10/2010 | Tumer | G01T 1/2985 | |
| | | | 250/363.03 | |
| 7,868,665 B2* | 1/2011 | Tümer et al. | H03F 3/087 | |
| | | | 327/509 | |
| 8,044,681 B2* | 10/2011 | Rao | G06G 7/18 | |
| | | | 250/208.1 | |
| 8,159,286 B2* | 4/2012 | Rao | G01T 1/2985 | |
| | | | 327/337 | |
| 8,170,175 B2* | 5/2012 | Kasuya | A61B 6/035 | |
| | | | 378/15 | |
| 8,198,577 B2* | 6/2012 | Dierickx | G01T 1/17 | |
| | | | 250/214 DC | |
| 8,213,566 B2* | 7/2012 | Roessl | A61B 5/4869 | |
| | | | 378/5 | |
| 8,258,480 B2* | 9/2012 | Olcott | G01T 1/1647 | |
| | | | 250/363.02 | |
| 8,260,565 B2* | 9/2012 | De Geronimo | G01R 19/0061 | |
| | | | 702/107 | |
| 8,269,180 B2* | 9/2012 | De Geronimo | G01T 1/247 | |
| | | | 250/370.01 | |
| 8,299,670 B2* | 10/2012 | Krumme | A61B 6/035 | |
| | | | 310/90 | |
| 8,338,773 B2* | 12/2012 | Eldesouki | G01J 1/46 | |
| | | | 250/208.1 | |
| 8,373,135 B2* | 2/2013 | Kappler | G01T 1/247 | |
| | | | 250/336.1 | |
| 8,378,310 B2* | 2/2013 | Bornefalk | G06T 11/005 | |
| | | | 250/370.01 | |
| 8,384,038 B2* | 2/2013 | Guo | G01T 1/247 | |
| | | | 250/370.09 | |
| 8,415,635 B2* | 4/2013 | Marks | G01T 1/171 | |
| | | | 250/370.09 | |
| 8,426,828 B2* | 4/2013 | Dierickx | G01J 1/44 | |
| | | | 250/371 | |
| 8,440,957 B2* | 5/2013 | Dierickx | G01T 1/247 | |
| | | | 250/214 R | |
| 8,491,190 B2* | 7/2013 | Glasser | G01T 1/247 | |
| | | | 378/207 | |
| 8,493,260 B2* | 7/2013 | Chu | H03M 1/14 | |
| | | | 341/163 | |
| 8,530,850 B2* | 9/2013 | Spartiotis | H01L 27/14634 | |
| | | | 250/370.08 | |
| 8,610,081 B2* | 12/2013 | Rao | G01T 1/247 | |
| | | | 250/394 | |
| 8,618,495 B2* | 12/2013 | De Geronimo | H03K 5/1532 | |
| | | | 250/395 | |
| 8,618,975 B2* | 12/2013 | Nys | H03M 1/144 | |
| | | | 341/172 | |
| 8,680,474 B2* | 3/2014 | Soh | H01L 27/14609 | |
| | | | 250/370.09 | |
| 8,692,176 B2* | 4/2014 | Kelly | G11B 20/00086 | |
| | | | 250/208.1 | |
| 8,716,643 B2* | 5/2014 | Eldesouki | H01L 27/14601 | |
| | | | 250/208.1 | |
| 8,729,485 B2* | 5/2014 | Soh | H04N 5/32 | |
| | | | 250/370.09 | |
| 8,748,832 B2* | 6/2014 | Brambilla | G01T 1/241 | |
| | | | 250/370.01 | |
| 8,766,198 B2* | 7/2014 | Dinapoli | G01T 1/243 | |
| | | | 250/370.01 | |
| 8,772,730 B2* | 7/2014 | Han | G01T 1/247 | |
| | | | 250/363.01 | |
| 8,816,290 B2* | 8/2014 | Hamlin | G01T 1/17 | |
| | | | 250/370.08 | |
| 8,816,292 B2* | 8/2014 | Cui | A61B 1/051 | |
| | | | 250/370.09 | |
| 8,859,944 B2* | 10/2014 | Eldesouki | H04N 5/3745 | |
| | | | 250/207 | |
| 8,866,094 B2* | 10/2014 | Tsukiyama | H04N 5/32 | |
| | | | 250/370.08 | |
| 8,866,097 B2* | 10/2014 | Meng | G01T 1/247 | |
| | | | 250/370.09 | |
| 8,866,662 B1 | 10/2014 | Naumov | | |
| 8,891,845 B2* | 11/2014 | Ogawa | A61B 6/14 | |
| | | | 382/128 | |
| 8,981,985 B2* | 3/2015 | Lian | H03M 1/1225 | |
| | | | 341/155 | |
| 8,988,267 B1* | 3/2015 | Kimura | G01T 1/2928 | |
| | | | 341/155 | |
| 9,014,455 B2* | 4/2015 | Oh | A61B 6/52 | |
| | | | 378/98.11 | |
| 9,029,793 B2* | 5/2015 | Spartiotis | H04N 5/32 | |
| | | | 250/370.09 | |
| 9,081,103 B2* | 7/2015 | Loeliger | G01T 1/171 | |
| 9,086,494 B2* | 7/2015 | Han | G01T 1/247 | |
| 9,116,249 B1* | 8/2015 | Claus | G01T 1/16 | |
| 9,121,955 B2* | 9/2015 | Schmitt | G01T 1/247 | |
| 9,128,195 B2* | 9/2015 | Soh | H04N 5/32 | |
| 9,185,314 B2 | 11/2015 | Mantri et al. | | |
| 9,213,108 B2* | 12/2015 | Nagai | A61B 6/4233 | |
| 9,239,391 B2* | 1/2016 | Han | G01T 1/17 | |
| 9,254,113 B2* | 2/2016 | Kim | A61B 6/4241 | |
| 9,274,235 B2* | 3/2016 | Kang | G01N 23/04 | |
| 9,297,912 B2* | 3/2016 | Campbell | G01T 1/247 | |
| 9,301,378 B2* | 3/2016 | Steadman Booker | G01T 1/24 | |
| 9,310,495 B2* | 4/2016 | Spartiotis | G01T 1/247 | |
| 9,351,701 B2* | 5/2016 | Yamakawa | A61B 6/025 | |
| 9,354,331 B2* | 5/2016 | Sagoh | A61B 6/032 | |

(56) References Cited

U.S. PATENT DOCUMENTS

| | | | |
|---|---|---|---|
| 9,417,339 B2* | 8/2016 | Spahn | G01T 1/247 |
| 9,437,771 B2* | 9/2016 | Deptuch | H01L 31/115 |
| 9,444,344 B2* | 9/2016 | Kim | G01T 1/247 |
| 9,461,664 B2* | 10/2016 | Sampath | H03M 1/442 |
| 9,517,045 B2* | 12/2016 | Kang | G01N 23/087 |
| 9,538,107 B2* | 1/2017 | Chappo | A61B 6/032 |
| 9,588,238 B2* | 3/2017 | Kim | G01T 1/247 |
| 9,588,239 B2* | 3/2017 | Abraham | G01T 1/247 |
| 9,595,101 B2* | 3/2017 | Kato | G06T 11/005 |
| 9,599,730 B2* | 3/2017 | Spahn | G01T 1/247 |
| 9,602,747 B2* | 3/2017 | Scott | H04N 5/378 |
| 9,608,652 B2* | 3/2017 | Lee | H03M 1/002 |
| 9,664,797 B2* | 5/2017 | Roessl | G01T 1/171 |
| 9,664,798 B2* | 5/2017 | Kappler | G01T 1/17 |
| 9,678,220 B2* | 6/2017 | Herrmann | G01T 1/17 |
| 9,696,432 B2* | 7/2017 | Ouvrier Buffet | G01T 1/17 |
| 9,700,268 B2* | 7/2017 | Kang | A61B 6/542 |
| 9,702,758 B2* | 7/2017 | Nouri | G01J 1/44 |
| 9,730,665 B2* | 8/2017 | Choi | A61B 6/5264 |
| 9,736,398 B2* | 8/2017 | Kim | G01T 1/17 |
| 9,750,471 B2* | 9/2017 | Schirra | A61B 6/4241 |
| 9,753,160 B2* | 9/2017 | Bellazzini | G01T 1/247 |
| 9,759,822 B2* | 9/2017 | Daerr | G01T 1/247 |
| 9,806,552 B2 | 10/2017 | Brannick et al. | |
| 9,952,333 B2* | 4/2018 | Abraham | G01T 1/17 |
| 9,958,557 B2* | 5/2018 | Kim | G01T 1/17 |
| 2008/0186214 A1 | 8/2008 | Janakiraman | |
| 2009/0046181 A1 | 2/2009 | Olsen et al. | |
| 2013/0076554 A1 | 3/2013 | Chu et al. | |
| 2013/0106629 A1 | 5/2013 | Nys et al. | |
| 2014/0232582 A1 | 8/2014 | Lian et al. | |
| 2015/0146055 A1 | 5/2015 | Sampath | |
| 2016/0079994 A1 | 3/2016 | Lee et al. | |
| 2017/0119325 A1 | 5/2017 | Tamura | |
| 2017/0160129 A1 | 6/2017 | Viswanath et al. | |
| 2018/0049707 A1 | 2/2018 | Ishitsu et al. | |

* cited by examiner

LOW POWER PHOTON COUNTING SYSTEM

CROSS REFERENCES TO RELATED APPLICATIONS

This application claims priority from India provisional patent application No. 4090/CHE/2015 filed on Aug. 6, 2015 which is hereby incorporated by reference in its entirety.

TECHNICAL FIELD

The present disclosure is generally related to medical diagnostic devices, and more particularly to a low power photon counting system in computed tomography (CT) data acquisition systems.

BACKGROUND

Computed tomography (CT) is a medical imaging technique that produces three-dimensional images of internal human body parts from a large series of two-dimensional X-ray images (called profiles) taken in a single-axis rotating structure called a gantry. When compared to a conventional X-ray radiograph, which is an image of many planes superimposed on each other, a CT image exhibits significantly improved contrast.

With the advent of diagnostic imaging systems like CT, where complex and intensive image processing is required, semiconductors play a very important role in developing systems with increased density, flexibility and high performance. The helical or spiral CT machines that use faster computer systems and optimized software can continuously process the cross-section images while the object passes through the gantry at a constant speed.

X-ray slice data is generated using an X-ray source that rotates around the object, with X-ray detectors positioned on the opposite side of the circle from the X-ray source. Many data scans are taken progressively as the patient/object is gradually passed through the gantry. A data acquisition system includes a plurality of detectors or channels.

A detector receives the x-rays attenuated by the patient and generates a corresponding current signal which is further converted to a digital signal. The existing CT systems also utilize spectral information embedded in the received x-rays. Some detectors of the plurality of detectors includes a photon counting system to derive the spectral information. The spectral information represents a variation in the energy (or energy resolution) of the photons received by a detector. The existing photon counting systems include an amplifier of high bandwidth to obtain the spectral information. However, a large amount of power is required to drive the amplifier and to meet a given noise specification. In addition, multiple static comparators are required in the existing photon counting systems which require large power for good energy resolution.

SUMMARY

According to an aspect of the disclosure, a circuit is disclosed. The circuit includes a charge sensitive amplifier (CSA) that generates an integrated signal in response to a current signal. An active comparator is coupled to the CSA. The active comparator receives the integrated signal and a primary reference voltage signal, and generates an event detect signal. A first delay element is coupled to the active comparator and provides a fixed delay to the event detect signal to generate a convert signal. A discriminator system is coupled to the CSA. The discriminator system samples the integrated signal when activated by the convert signal.

DETAILED DESCRIPTION OF THE EMBODIMENTS

Figure 1:
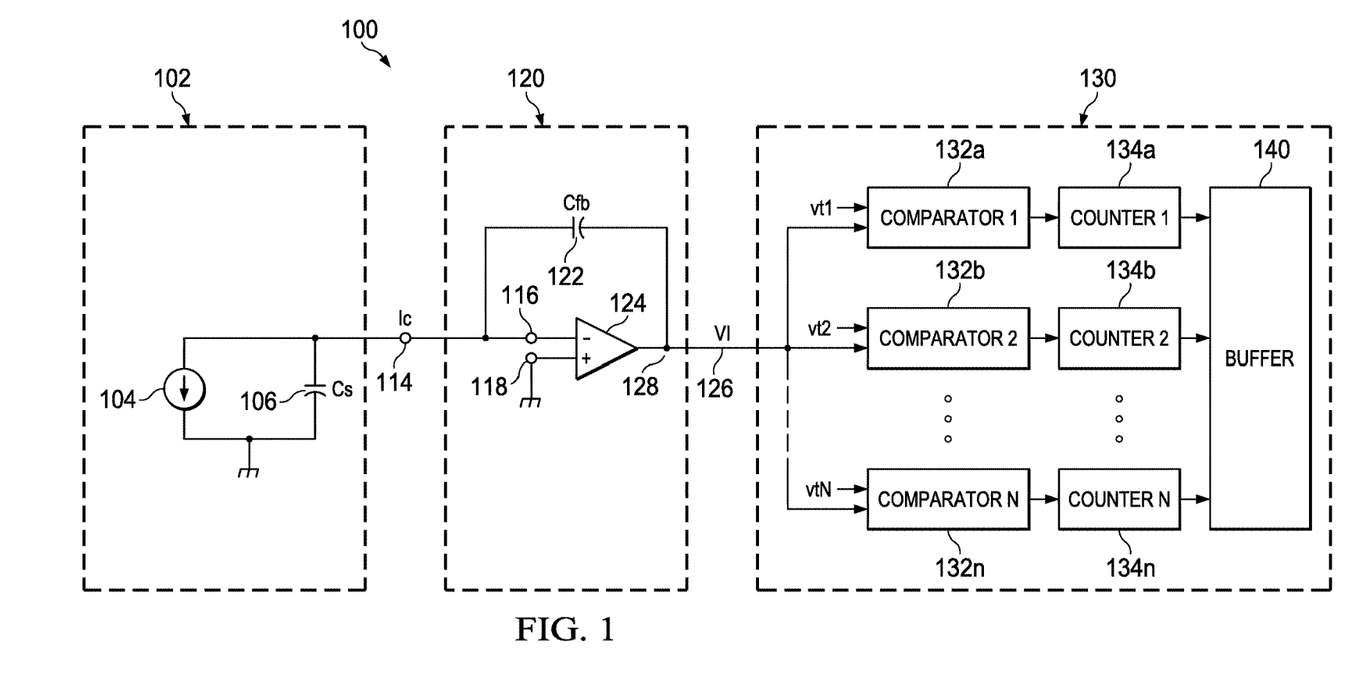
FIG. 1 illustrates a circuit.

FIG. 1 illustrates a circuit 100. The circuit 100 includes a photodiode 102, a charge sensitive amplifier (CSA) 120 and a discriminator system 130. The photodiode 102 includes a sensor 104 and an associated capacitance Cs 106. The CSA 120 is coupled to the photodiode 102. The CSA 120 includes a primary transconductor 124 with an inverting terminal 116, a non-inverting terminal 118 and an output terminal 128. The photodiode 102 is coupled to the inverting terminal 116 of the primary transconductor 124. The non-inverting terminal 118 is coupled to a ground terminal. A feedback capacitor Cfb 122 is coupled between the inverting terminal 116 and the output terminal 128 of the primary transconductor 124.

The discriminator system 130 is coupled to the CSA 120. The discriminator system 130 includes one or more comparators illustrated as comparator 1 132*a*, comparator2 132*b* to comparatorN 132*n*. The one or more comparators in the discriminator system 130 are coupled to the output terminal 128 of the primary transconductor 124. The one or more comparators receive one or more threshold voltages represented as Vt1, Vt2, to VtN. For example, the comparator1 132*a* receives the threshold voltage Vt1, and the comparatorN 132*n* receives the threshold voltage VtN. The discriminator system 130 also includes one or more counters illustrated as counter1 134*a*, counter2 134*b*, to counterN 134*n*. The one or more counters are coupled to the one or more comparators. For example, counter1 134*a* is coupled to the comparator1 132*a*, and counter2 134*b* is coupled to the comparator 132*b*. A buffer 140 is coupled to the one or more counters.

The operation of the circuit 100 illustrated in FIG. 1 is explained now. The photodiode 102 receives light which includes multiple photons of different energies. The photodiode 102 generates a corresponding current signal Ic 114. The sensor 104 receives the light, and the associated capacitance Cs 106 stores a charge corresponding to the received light. The current signal Ic 114 generated by the photodiode 102 is received by the CSA 120. The CSA 120 generates an integrated signal VI 126 in response to the current signal Ic 114. The integrated signal VI 126 is generated at the output terminal 128 of the primary transconductor 124. Each comparator of the one or more comparators in the discriminator system 130 receives the integrated signal VI 126.

A counter of the one or more counters is coupled to a comparator, increases its count when the integrated signal VI 126 received by the comparator is above a threshold voltage received by the comparator. For example, the counter1 134*a* increases its count when the integrated signal VI 126 received by the comparator1 132*a* is above the threshold voltage Vt1. Similarly, the counterN 134*n* increases its count when the integrated signal VI 126 received by the comparatorN 132*n* is above the threshold voltage VtN. The buffer 140 in the discriminator system 130 stores the count of each counter of the one or more counters.

When the light that includes multiple photons is received by the photodiode 102, the corresponding current signal Ic 114 is generated. The CSA 120 generates the integrated signal VI 126 in response to the current signal Ic 114. Each comparator of the one or more comparators in the discriminator system 130 receives the integrated signal VI 126. Each comparator compares the integrated signal VI 126 with a threshold voltage. For example, the comparator1 132*a* compares the integrated signal VI 126 and the threshold voltage Vt1. When the integrated signal VI 126 is greater than the threshold voltage Vt1, a count of the counter1 134*a* is increment by 1. In one example, the one or more threshold voltages Vt1, Vt2 to VtN are provided in incremental order i.e. VtN is a highest threshold voltage and Vt1 is a lowest threshold voltage. Thus, Vt2 is greater than Vt1, and VtN is greater than Vt1 and Vt2. For example, Vt1 is 20 keV, Vt2 is 40 keV and VtN is 100 keV. In one version, when a photon of energy 120 keV is received by the circuit 100, each of the counter of the one or more counters is incremented, since 120 keV is greater than Vt1 (20 keV), Vt2 (40 keV) and VtN (100 keV). In another version, only the counterN 134*n* is incremented when the photon of energy 120 keV is received. In this version, the counter1 134*a* is incremented when a photon of energy 0-20 keV is received, and counter2 134*b* is incremented when a photon of energy 20 keV to 40 keV is received.

Thus, a combination of the comparator and the counter acts as an energy bin. For example, the comparator1 132*a* and the counter1 134*a* act as an energy bin, and the comparator2 132*b* and the counter2 134*b* acts as an another energy bin. The circuit 100 is able to classify the photons in different energy bins. The count of a number of photons by one or more counters in the discriminator system 130 provides spectral information. The spectral information is a variation in the energy of the photons received by the photodiode 102.

However, the CSA 120 is a high bandwidth amplifier, and hence, a large amount of power is required to drive the CSA 120. For better energy resolution, multiple comparators are required in the discriminator system 130 which proportionately increases power consumption of the circuit 100. Also, the photons received by the photodiode 102 are asynchronous in nature. It is difficult to count all photons received by the photodiode 102 using the CSA 120 because of finite bandwidth. A dead time of the circuit 100 is defined as a minimum separation required in time between two received photons so that they can be recorded distinctly by the circuit 100. However, the dead time of the circuit 100 drifts with temperature. Also, the dead time of the circuit 100 measured at a time of calibrating the circuit 100 is different from a time at which the circuit 100 is put to actual use. This causes an error in calculating a number of photons received by the circuit 100. Thus, when circuit 100 is part of a Computed tomography (CT) system, it results in an error in reconstruction of an image.

High energy photons cause a large current signal Ic 114 to be generated in the circuit 100. This causes a large integrated signal VI 126 to be generated at the output terminal 128. This causes a large dead time for high energy photons and a small dead time for low energy photons. This introduces artifacts in the image reconstructed in the CT system. Thus, a varying dead time degrades the performance of the circuit 100.

Figure 2:
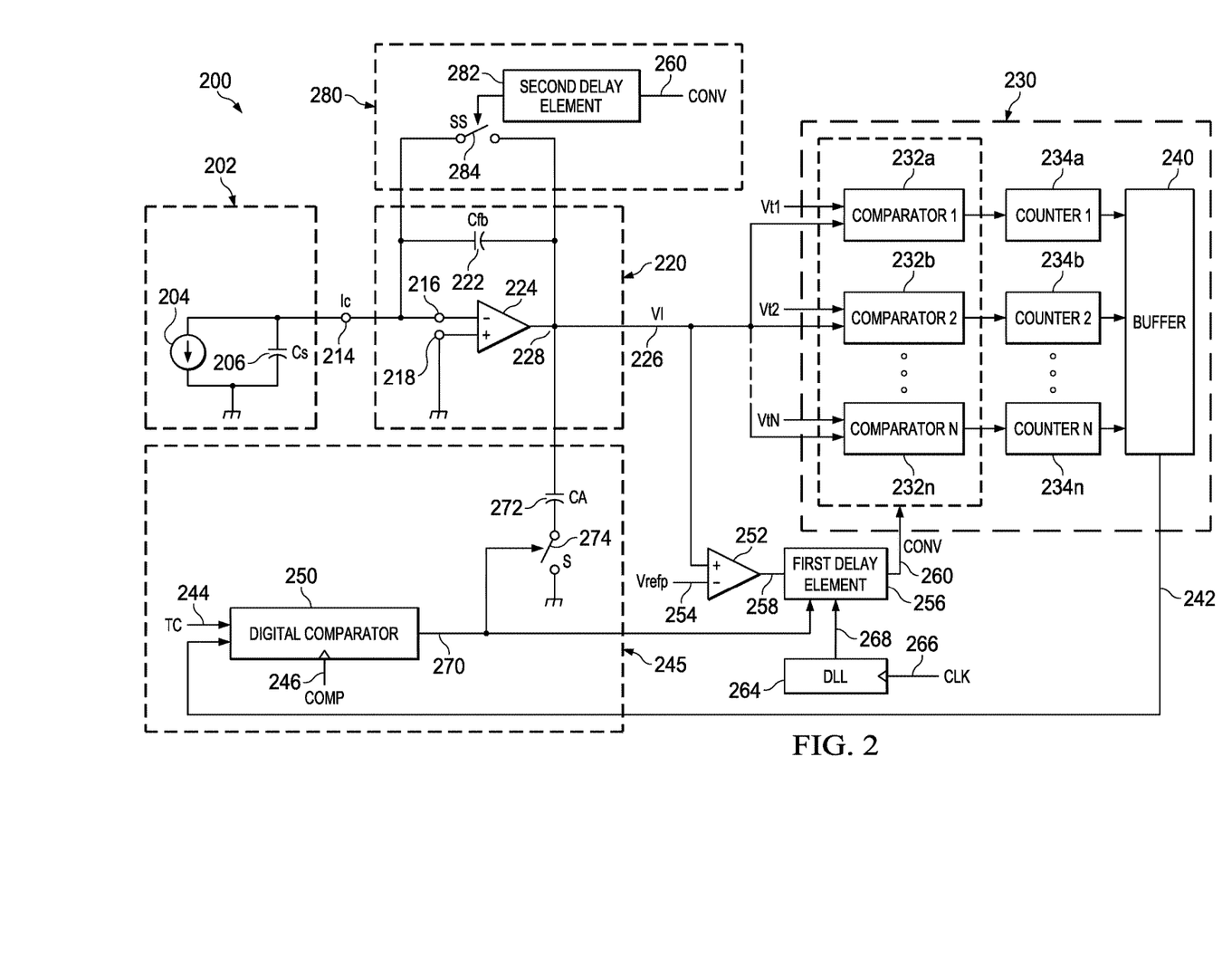
FIG. 2 illustrates a circuit, according to an embodiment.

FIG. 2 illustrates a circuit 200, according to an embodiment. The circuit 200, in one application, is a photon counting system. The circuit 200 includes a photodiode 202. In one version, the photodiode 202 is a direct converter photodiode. The photodiode 202 includes a sensor 204 and an associated capacitance Cs 206. A charge sensitive amplifier (CSA) 220 is coupled to the photodiode 202. The CSA 220 includes a primary transconductor 224 with an inverting terminal 216, a non-inverting terminal 218 and an output terminal 228. The photodiode 202 is coupled to the inverting terminal 216 of the primary transconductor 224. The non-inverting terminal 218 is coupled to a ground terminal. A feedback capacitor Cfb 222 is coupled between the inverting terminal 216 and the output terminal 228 of the primary transconductor 224.

A discriminator system 230 is coupled to the CSA 220. The discriminator system 230 includes one or more comparators illustrated as comparator1 232*a*, comparator2 232*b* to comparatorN 232*n*. The one or more comparators in the discriminator system 230 are coupled to the output terminal 228 of the primary transconductor 224. The one or more comparators receive one or more threshold voltages represented as Vt1, Vt2 to VtN. For example, the comparator1 232*a* receives the threshold voltage Vt1, and the comparatorN 232*n* receives the threshold voltage VtN. The discriminator system 230 also includes one or more counters illustrated as counter1 234*a*, counter2 234*b* to counterN 234*n*. The one or more counters are coupled to the one or more comparators. For example, counter1 234*a* is coupled to the comparator1 232*a*, and counter2 234*b* is coupled to the comparator2 232*b*. A buffer 240 is coupled to the one or more counters.

The circuit 200 also includes an active comparator 252. The active comparator 252 is coupled to the output terminal 228 of the primary transconductor 224. The active comparator 252 also receives a primary reference voltage signal Vrefp 254. A first delay element 256 is coupled to the active comparator 252. The first delay element 256 is also coupled to the one or more comparators in the discriminator system 230. A delay locked loop (DLL) 264 is coupled to the first delay element 256. The DLL 264 receives a clock signal CLK 266.

The circuit 200 also includes a bandwidth control circuit 245. The bandwidth control circuit 245 is coupled between the output terminal 228 of the primary transconductor 224 and the first delay element 256. The bandwidth control circuit 245 includes a digital comparator 250. The digital comparator 250 is coupled to the buffer 240 and receives a threshold count TC 244. The bandwidth control circuit 245 also includes an additional capacitor CA 272 and a switch S 274. The additional capacitor CA 272 is coupled to the output terminal 228 of the primary transconductor 224. The switch S 274 is coupled between the additional capacitor CA 272 and a ground terminal. The switch S 274 is also coupled to the digital comparator 250. The first delay element 256 is coupled to the digital comparator 250.

The circuit 200 includes a reset switch 280 coupled in parallel to the CSA 220. The reset switch 280 includes a second delay element 282 and a secondary switch SS 284. The secondary switch SS 284 is coupled in parallel to the feedback capacitor Cfb 222. The circuit 200 may include one or more additional components known to those skilled in the relevant art and are not discussed here for simplicity of the description.

The operation of the circuit 200 illustrated in FIG. 2 is explained now. The photodiode 202 receives light which includes multiple photons of different energies. The photodiode 202 generates a corresponding current signal Ic 214. The sensor 204 receives the light, and the associated capacitance Cs 206 stores a charge corresponding to the received light. The current signal Ic 214 generated by the photodiode 202 is received by the CSA 220. The CSA 220 generates an integrated signal VI 226 in response to the current signal Ic 214. In one example, the CSA 220 integrates the current signal Ic 214 to generate the integrated signal VI 226. The integrated signal VI 226 is generated at the output terminal 228 of the primary transconductor 224.

The active comparator 252 receives the integrated signal VI 226 from the CSA 220. The active comparator 252 compares the integrated signal VI 226 and the primary reference voltage signal Vrefp 254 to generate an event detect signal 258. The first delay element 256 provides a fixed delay to the event detect signal 258 and generates a convert signal CONV 260. The DLL 264 receives the clock signal CLK 266. The DLL 264 provides a controlled voltage 268 to the first delay element 256. The fixed delay is a function of the controlled voltage 268. The controlled voltage 268 is a function of a time period of the clock signal CLK 266.

The discriminator system 230 samples the integrated signal VI 226 when activated by the convert signal CONV 260. Each comparator of the one or more comparators in the discriminator system 230 receives the integrated signal VI 226 and a threshold voltage of the one or more threshold voltages. When the discriminator system 230 is activated by the convert signal CONV 260, each comparator compares the integrated signal VI 226 and a threshold voltage.

A counter of the one or more counters coupled to a comparator, increases its count when the integrated signal VI 226 received by the comparator is above a threshold voltage received by the comparator. For example, the counter1 234a increases its count when the integrated signal VI 226 received by the comparator1 232a is above the threshold voltage Vt1. Similarly, the counterN 234n increases its count when the integrated signal VI 226 received by the comparatorN 232n is above the threshold voltage VtN. The buffer 240 in the discriminator system 230 buffers or stores the count of each counter of the one or more counters. In one example, the buffer 240 sums the count of all the counters to generate a total photon count 242.

The reset switch 280 resets the CSA 220 when activated by the convert signal CONV 260. The second delay element 282 receives the convert signal CONV 260. The convert signal CONV 260 is delayed by the second delay element 282 to generate a reset signal. The reset signal activates the secondary switch SS 284 which resets the CSA 220.

The digital comparator 250 in the bandwidth control circuit 245 receives the total photon count 242. The digital comparator 250 also receives the threshold count TC 244. The digital comparator 250 generates a bandwidth control signal 270 when the total photon count 242 is less than the threshold count TC 244. The bandwidth control signal 270 activates the switch S 274, which couples the additional capacitor CA 272 to the ground terminal. The first delay element receives the bandwidth control signal 270 and provides an additional delay to the event detect signal 258 to generate the convert signal CONV 260. The additional delay is greater than the fixed delay.

The digital comparator 250 receives the total photon count in a first cycle, and the digital comparator 250 generates the bandwidth control signal 270 in a second cycle. The digital comparator 250 is activated by a compare signal COMP 246 to generate the bandwidth control signal 270. The compare signal COMP 246 is provided to the digital comparator 250 at an end of the first cycle and before beginning of the second cycle. The second cycle occurs after the first cycle. The bandwidth control circuit 245 utilizes a fact that a number of photons received by the photodiode 202 (or by a CT system with the circuit 200) changes gradually. Thus, with knowledge of the total photon count 242 in a previous cycle, a region of operation of the circuit is determined. When the total photon count 242 is less than the threshold count TC 244, the circuit 200 is operating in a low intensity region. When the total photon count 242 is greater than the threshold count TC 244, the circuit 200 is operating in a high intensity region. Thus, when the total photon count 242 is less than the threshold count TC 244 i.e. the circuit 200 is operating in the low intensity region, the switch S 274 is activated such that the additional capacitor CA 272 is coupled to the ground terminal. This reduces a bandwidth of the CSA 220 and hence reduces a noise in the circuit 200. As a result, no additional power is required to reduce the noise of the circuit 200 when the circuit 200 is operating in the low intensity region.

In one example, the digital comparator 250 receives the total photon count 242 in the first cycle and generates the bandwidth control signal 270 in the second cycle when the total photon count 242 is less than the threshold count TC 244. The first cycle and the second cycle are consecutive cycles with second cycle occurring after the first cycle. In one version, the first cycle is a past cycle and the second cycle is a current cycle. In another version, a cycle is a time period of operation of the circuit 200 in which the photodiode 202 receives an influx of photons.

When the light that includes multiple photons is received by the photodiode 202, a corresponding current signal Ic 214 is generated. The CSA 220 generates the integrated signal VI 226 in response to the current signal Ic 214. The active comparator 252 is always active while the one or more comparators in the discriminator system 230 are activated only on receiving the convert signal CONV 260 from the first delay element 256. This results in a significant power savings in the circuit 200 as compared to the circuit 100.

In one example, the active comparator 252 does not generate the event detect signal 258 when the integrated signal VI 226 is less than the primary reference voltage signal Vrefp 254. The active comparator 252 toggles or generates the event detect signal 258 when the integrated signal VI 226 is greater than the primary reference voltage signal Vrefp 254. The first delay element 256 delays the event detect signal 258 by the fixed delay to generate the convert signal CONV 260. The fixed delay is a function of the controlled voltage 268 received from the DLL 264. In a condition, when the first delay element 256 receives the bandwidth control signal 270 from the digital comparator 250, the first delay element 256 delays the event detect signal 258 by the additional delay to generate the convert signal CONV 260. The additional delay is greater than the fixed delay. The fixed delay is equal to the dead time of the circuit 200. Thus, the active comparator 252 and the first delay element 256 ensures a constant dead time for the circuit 200. The dead time of the circuit 200 is defined as a minimum separation required in time between two received photons so that they can be recorded distinctly by the circuit 200. The circuit 200 is ready to detect a new photon immediately after the CSA 220 is reset. Thus, the dead time of the circuit 200 is maintained constant by the active comparator 252 and the first delay element 256.

The discriminator system 230 is activated on receiving the convert signal CONV 260. On receiving the convert signal CONV 260, the one or more comparators in the discriminator system 230 are activated. Each comparator of the one or more comparators in the discriminator system 230 receives the integrated signal VI 226. Each comparator compares the integrated signal VI 226 with a threshold voltage. For example, the comparator1 232a compares the integrated signal VI 226 and the threshold voltage Vt1. When the integrated signal VI 226 is greater than the threshold voltage Vt1, a count of the counter1 234a is increment by 1. In one example, the one or more threshold voltages Vt1, Vt2 to VtN are provided in incremental order i.e. VtN is a highest threshold voltage and Vt1 is a lowest threshold voltage. Thus, Vt2 is greater than Vt1, and VtN is greater than Vt1 and Vt2. For example, Vt1 is 20 keV, Vt2 is 40 keV and VtN is 200 keV. In one version, when a photon of energy 220 keV is received by the circuit 200, each of the counter of the one or more counters is incremented, since 220 keV is greater than Vt1 (20 keV), Vt2 (40 keV) and VtN (200 keV). In another version, only the counterN 234n is incremented when the photon of energy 220 keV is received. In this version, the counter1 234a is incremented when a photon of energy 0-20 keV is received, and the counter2 234b is incremented when a photon of energy 20 keV to 40 keV is received. The energy values (in keV) are provided to explain the logical flow of methods and are understood not to limit the scope of the present disclosure.

Thus, a combination of the comparator and the counter acts as an energy bin. For example, the comparator1 232a and the counter1 234a act as an energy bin, and the comparator2 232b and the counter2 acts as an another energy bin. The circuit 200 is able to classify the photons in different energy bins. The count of a number of photons by one or more counters in the discriminator system 230 provides spectral information. The spectral information is a variation in the energy of the photons received by the photodiode 202. The buffer 240 sums the count of each counter of the one or more counters to generate the total photon count 242.

The discriminator system 230 samples the integrated signal VI 226 when activated by the convert signal CONV 260. The second delay element 282 delays the convert signal CONV 260 and resets the CSA 220. The circuit 200 thus provides a mechanism to activate the discriminator system 230 only when sampling of the integrated signal VI 226 is required. This provides significant power saving in the circuit 200. The DLL 264 is used to provide a constant dead time to the circuit 200. The bandwidth control circuit 245 reduces the bandwidth of the CSA 220 in low intensity region and hence reduces a noise in the circuit 200.

Figure 3:
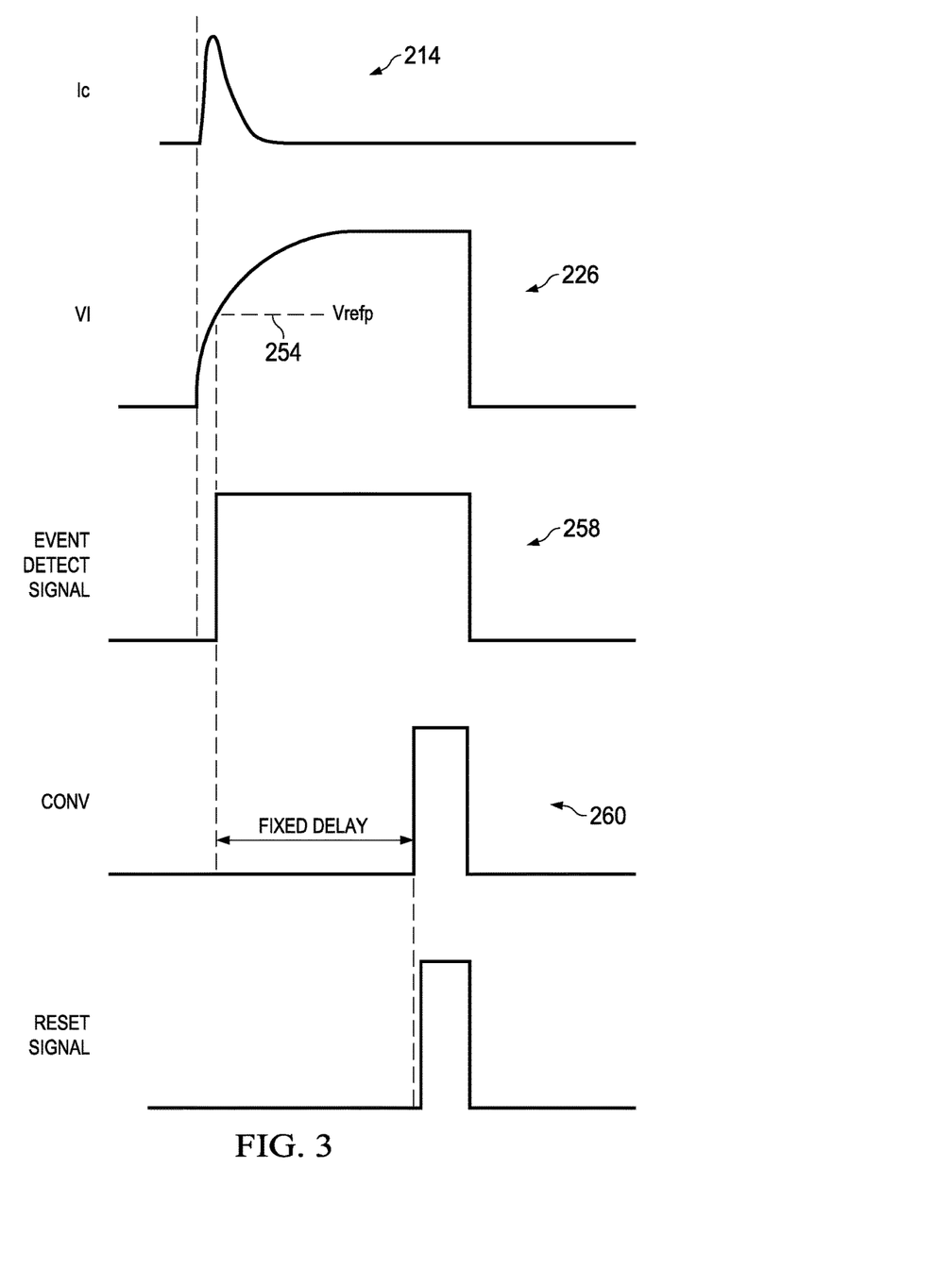
FIG. 3 is a timing diagram to illustrate operation of a circuit, according to an embodiment.

FIG. 3 is a timing diagram to illustrate operation of a circuit, according to an embodiment. The timing diagram illustrates operation of the circuit 200. The figure illustrates the current signal Ic 214, the integrated signal VI 226, the event detect signal 258, the convert signal CONV 260 and the reset signal generated by the second delay element 282. The CSA 220 integrates the current signal Ic 214 to generate the integrated signal VI 226. The event detect signal 258 is generated when the integrated signal VI 226 is greater than the primary reference voltage signal Vrefp 254.

The first delay element 256 delays the event detect signal 258 by the fixed delay to generate the convert signal CONV 260. The fixed delay is a function of the controlled voltage 268 received from the DLL 264. The controlled voltage depends on a time period of the clock signal CLK 266. In a condition, when the first delay element 256 receives the bandwidth control signal 270 from the digital comparator 250, the first delay element 256 delays the event detect signal 258 by the additional delay to generate the convert signal CONV 260. The additional delay is greater than the fixed delay. In this condition, the additional delay is equal to the dead time of the circuit 200. Thus, the active comparator 252 and the first delay element 256 ensures a constant dead time for the circuit 200.

The discriminator system 230 is activated on receiving the convert signal CONV 260. The discriminator system 230 samples the integrated signal VI 226 on receiving the convert signal CONV 260. The second delay element 282 delays the convert signal CONV 260 to generate the reset signal. As illustrated in the FIG. 3, the convert signal CONV 260 is delayed by a small time after which the reset signal is generated. This time allows the discriminator system 230 to sample the integrated signal VI 226. The reset signal resets the CSA 220. This ensures a constant dead time of the circuit 200.

Figure 4A:
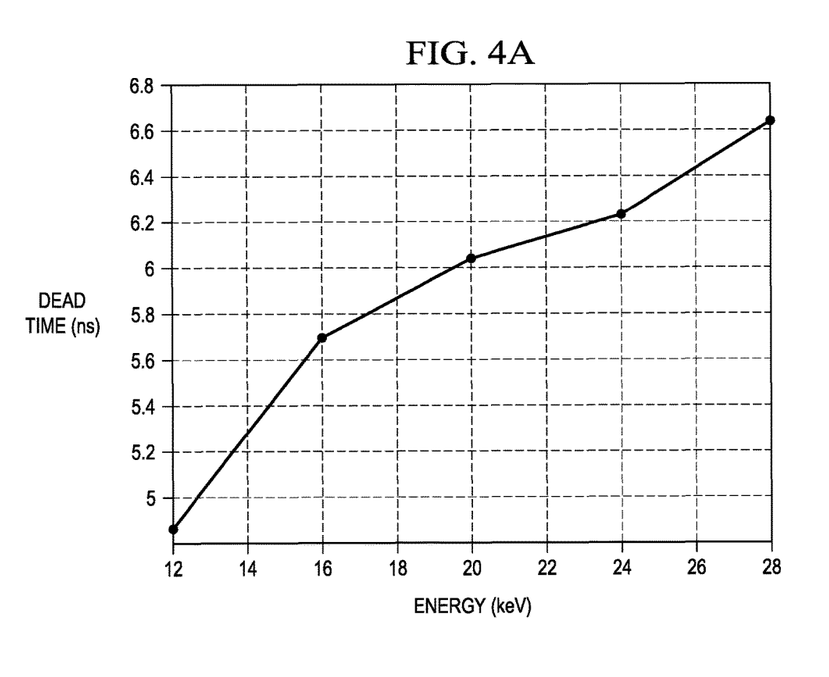
FIG. 4(A) and FIG. 4(B) are graphs to illustrate variation of dead time with energy of photons, according to an embodiment.
Figure 4B:
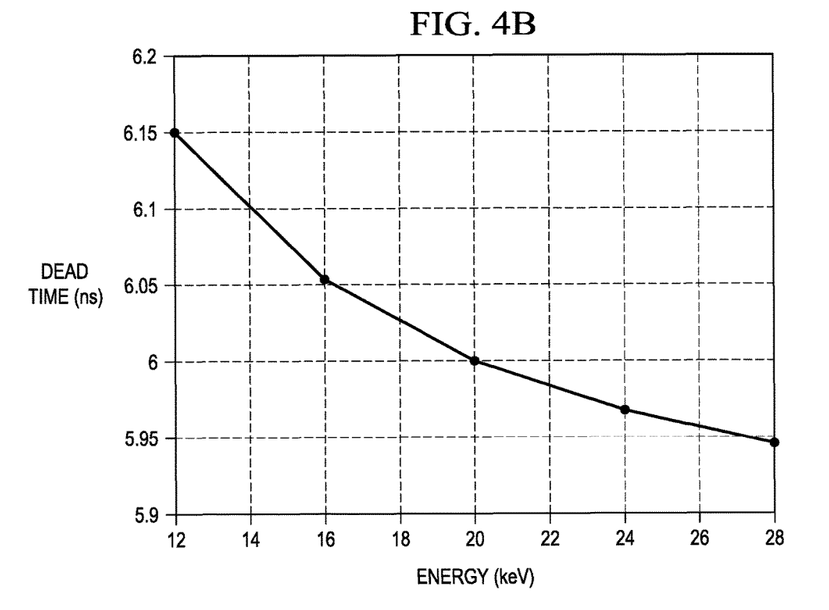

FIG. 4(A) and FIG. 4(B) are graphs to illustrate variation of dead time with energy of incident photons, according to an embodiment. The FIG. 4(A) illustrates dead time variation with energy of photons in circuit 100, while FIG. 4(B) illustrates dead time variation with energy of photons in circuit 200.

The FIG. 4(A) illustrates that as the energy of the photons received by the circuit 100 increases, the dead time also increases. Thus, high energy photons cause a large current to be generated in the circuit 100. This causes a large integrated signal VI 126 to be generated at the output terminal 128 of the circuit 100. This causes a large dead time for large energy photons. The circuit 100 provides a small dead time for low energy photons. This introduces image artifacts in an image reconstructed in a CT system with the circuit 100. The FIG. 4(B) illustrates that as the energy of the photons received by the circuit 200 increases, the dead time decreases.

A variation (minimum value to maximum value) in the dead time of the circuit 200 (as seen in FIG. 4(B)) is smaller than a variation in the dead time of the circuit 100 (as seen in FIG. 4(A)). In circuit 100, the integrated signal VI 126 decays with an RC time constant. As a result, a time taken for the integrated signal VI 126 to cross a fixed threshold in a negative direction is proportional to the energy of the photons. In circuit 200, the integrated signal VI 226 is reset immediately after a fixed delay which defines the dead time of the circuit 200. Therefore, the dead time in the circuit 200 is independent of the energy of the photons. The active comparator 252 and the first delay element 256 ensures a constant dead time of the circuit 200.

Figure 5:
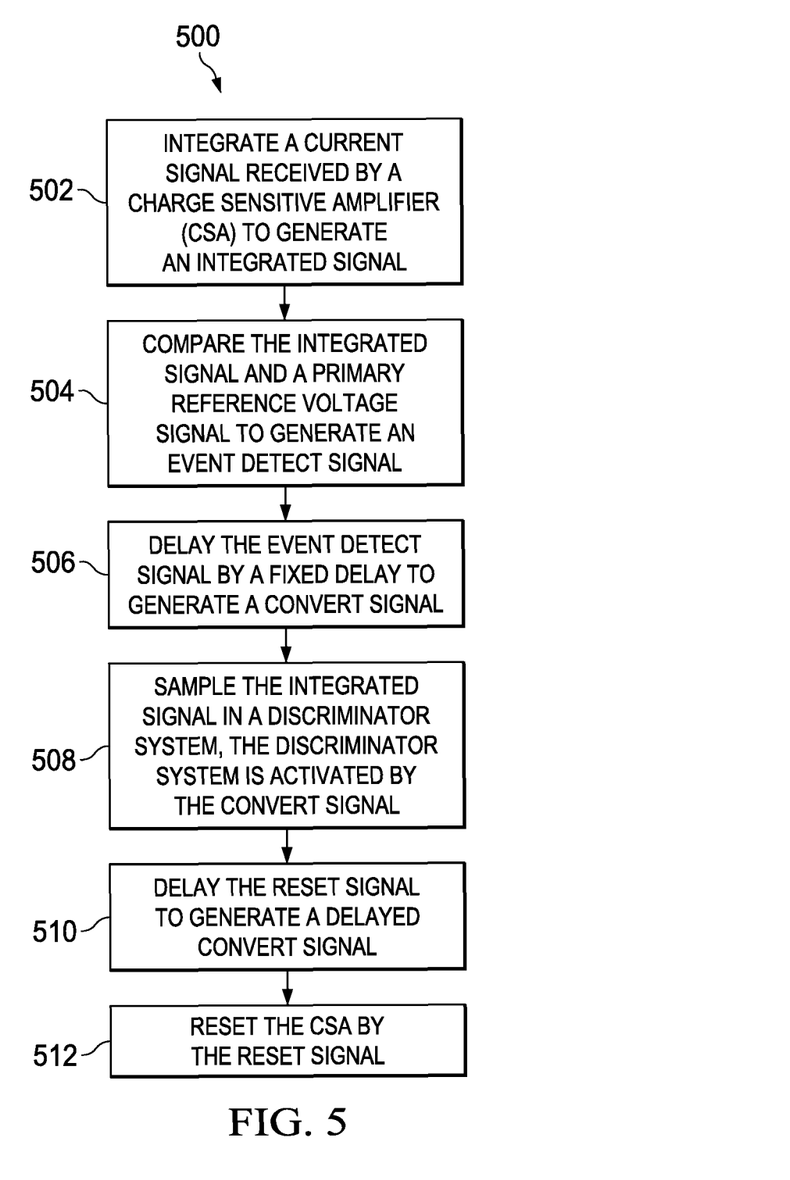
FIG. 5 is a flowchart to illustrate a method of operation of a circuit, according to an embodiment.

FIG. 5 is a flowchart 500 to illustrate a method of operation of a circuit, according to an embodiment. The flowchart 500 is explained in connection with the circuit 200. At step 502, a current signal Ic 214 received by a charge sensitive amplifier (CSA) 220 is integrated to generate an integrated signal VI 226. For example, in circuit 200, the current signal Ic 214 is integrated to generate the integrated signal VI 226. At step 504, the integrated signal VI 226 and a primary reference voltage signal Vrefp 254 are compared to generate an event detect signal 258. In one version, the event detect signal 258 is generated when the integrated signal VI 226 is greater than the primary reference voltage signal Vrefp 254.

The event detect signal 258 is delayed by a fixed delay to generate a convert signal CONV 260, at step 506. In circuit 200, the first delay element 256 delays the event detect signal 258 by the fixed delay to generate the convert signal CONV 260. The fixed delay is a function of the controlled voltage 268 received from the DLL 264. The fixed delay ensure a constant dead time for the circuit 200. A dead time of the circuit 200 is defined as a minimum separation required in time between two received photons so that they can be recorded distinctly by the circuit 200.

At step 508, a discriminator system 230 is activated on receiving the convert signal CONV 260. The integrated signal VI 226 is sampled in the discriminator system 230. On receiving the convert signal CONV 260, the one or more comparators in the discriminator system 230 are activated. The discriminator system 230 is activated only when sampling of the integrated signal VI 226 is required. This provides significant power saving in the circuit 200. At step 510, the convert signal CONV 260 is delayed to generate a reset signal, and at step 512 the CSA 220 is reset by the reset signal. In circuit 200, the reset switch 280 resets the CSA 220 when activated by the convert signal CONV 260. The second delay element 282 receives the convert signal CONV 260. The convert signal CONV 260 is delayed by the second delay element 282 to generate a reset signal. The reset signal activates the secondary switch SS 284 which resets the CSA 220.

Figure 6:
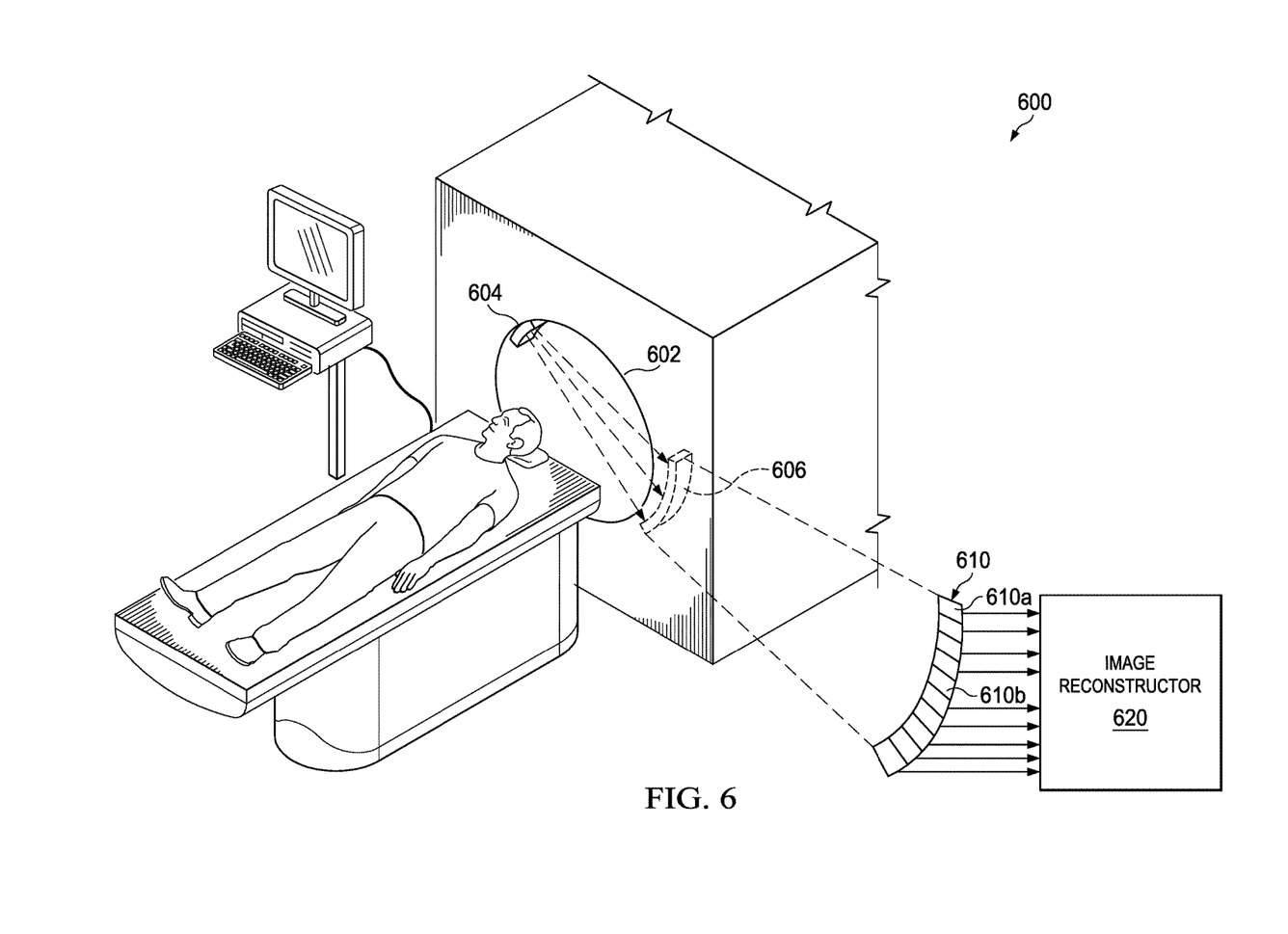
FIG. 6 illustrates an imaging system, according to an embodiment.

FIG. 6 illustrates an imaging system 600, according to an embodiment. The imaging system 600, in one version, is a CT (computed tomography) imaging system. The imaging system 600 includes a gantry 602 that receives a patient. The gantry 602 rotates at a defined speed. In one example, a controller provides the defined speed to the gantry 602.

An x-ray source 604 is disposed in the gantry 602. The x-ray source 604 emits x-rays towards the patient. The x-rays are attenuated by the patient and received by a receiver 606. Many scans are taken progressively as the patient/object is gradually passed through the gantry 602. A cross-section of the receiver 606 is enlarged and illustrated for better clarity. The cross-section includes a plurality of detectors 610.

The plurality of detectors 610 receives x-rays attenuated by the patient. The plurality of detectors 610 includes detectors 610a and 610b. At least one detector of the plurality of detectors 610 generates a current signal in response to the received attenuated x-rays. The at least one detector is similar to the circuit 200 (illustrated in FIG. 2) in connection and operation. In one example, the detector 610b is similar to the circuit 200 in connection and operation. The photodiode in the detector 610b generates the current signal in response to the received attenuated x-rays from the patient. The detector 610b generates an integrated signal in response to the current signal. The integrated signal is sampled by a discriminator system in the detector 610b. However, the discriminator system samples the integrated signal when activated by a convert signal.

This ensures a constant dead time of the detector 610b. The detector 610b thus provides a mechanism to activate the discriminator system only when sampling of the integrated signal is required. This provides significant power saving in the detector 610b. The detector 610b includes a bandwidth control circuit similar to the bandwidth control circuit 245 (illustrated in FIG. 2) which reduces noise in the detector 610b.

The image reconstructor 620 receives the digital signal from each detector of the plurality of detectors 610 to create an image of a part of patient which is being scanned by the imaging system 600. The image reconstructor 620, in one example, includes a processor. The processor can be, for example, a CISC-type (Complex Instruction Set Computer) CPU, RISC-type CPU (Reduced Instruction Set Computer), or a digital signal processor (DSP). The image reconstructor 620, in one example, is disposed outside the imaging system 600. The imaging system 600 may include one or more additional components known to those skilled in the relevant art and are not discussed here for simplicity of the description.

The foregoing description sets forth numerous specific details to convey a thorough understanding of the invention. However, it will be apparent to one skilled in the art that the invention may be practiced without these specific details. Well-known features are sometimes not described in detail in order to avoid obscuring the invention. Other variations and embodiments are possible in light of above teachings, and it is thus intended that the scope of invention not be limited by this Detailed Description, but only by the following Claims.

What is claimed is:

1. A circuit comprising:
    a charge sensitive amplifier (CSA) configured to generate an integrated signal in response to a current signal;
    an active comparator coupled to the CSA and configured to receive the integrated signal and a primary reference voltage signal, the active comparator configured to generate an event detect signal;
    a first delay element coupled to the active comparator and configured to provide a fixed delay to the event detect signal to generate a convert signal; and
    a discriminator system coupled to the CSA, wherein the discriminator system is configured to sample the integrated signal when activated by the convert signal.

2. The circuit of claim 1, further comprising a reset switch coupled in parallel to the CSA, wherein the reset switch resets the CSA when activated by the convert signal.

3. The circuit of claim 1, wherein the fixed delay is equal to a dead time of the circuit.

4. The circuit of claim 1, wherein the CSA comprises:
    a primary transconductor configured to receive the current signal at an inverting terminal, and configured to generate the integrated signal at an output terminal;
    a non-inverting terminal of the primary transconductor is coupled to a ground terminal; and
    a feedback capacitor coupled between the inverting terminal and the output terminal of the primary transconductor.

5. The circuit of claim 4, wherein the reset switch comprises:
    a second delay element configured to delay the convert signal to generate a reset signal; and
    a secondary switch coupled in parallel to the feedback capacitor, wherein the secondary switch is activated by the reset signal.

6. The circuit of claim 4, further comprising a bandwidth control circuit coupled between the output terminal of the primary transconductor and the first delay element, the bandwidth control circuit comprising:
    an additional capacitor coupled to the output terminal;
    a switch coupled between the additional capacitor and the ground terminal; and
    a digital comparator configured to receive the total photon count and a threshold count, the digital comparator configured to generate a bandwidth control signal when the total photon count is less than the threshold count, the bandwidth control signal is provided to the first delay element, and the bandwidth control signal is configured to activate the switch and the first delay element.

7. The circuit of claim 6, wherein the digital comparator receives the total photon count in a first cycle, and the digital comparator generates the bandwidth control signal when activated by a compare signal, the compare signal is provided to the digital comparator at an end of the first cycle and before beginning of a second cycle, the second cycle occurs after the first cycle.

8. The circuit of claim 6, wherein the first delay element on receiving the bandwidth control signal is configured to provide an additional delay to the event detect signal to generate the convert signal, the additional delay is greater than the fixed delay.

9. The circuit of claim 6, wherein when the total photon count is less than the threshold count, the circuit is operating in a low intensity region, and the bandwidth control signal activates the switch to couple the additional capacitor to the ground terminal.

10. The circuit of claim 1, wherein the discriminator system further comprises:
one or more comparators configured to receive the integrated signal and one or more threshold voltages;
one or more counters coupled to the one or more comparators, a counter of the one or more counters coupled to a comparator of the one or more comparators is configured to increment its count when the integrated signal received by the comparator is above a threshold voltage received by the comparator; and
a buffer coupled to the one or more counters, the buffer configured to store a count of each counter of the one or more counters and configured to generate a total photon count.

11. The circuit of claim 1, further comprising a delay locked loop (DLL) configured to receive a clock signal, the DLL configured to provide a controlled voltage to the first delay element, wherein the fixed delay is a function of the controlled voltage.

12. A method comprising:
integrating a current signal received by a charge sensitive amplifier (CSA) to generate an integrated signal;
comparing the integrated signal and a primary reference voltage signal to generate an event detect signal;
delaying the event detect signal by a fixed delay to generate a convert signal;
activating a discriminator system with the convert signal;
sampling the integrated signal in the discriminator system;
delaying the convert signal to generate a reset signal; and
resetting the CSA by the reset signal.

13. The method of claim 12, wherein sampling the integrated signal further comprises:
receiving the integrated signal by one or more comparators, the one or more comparator configured to receive one or more threshold voltages;
comparing the integrated signal with the one or more threshold voltages received by the one or more comparators, the one or more comparators are coupled to one or more counters;
incrementing a count of a counter of the one or more counters coupled to a comparator of the one or more comparators when the integrated signal received by the comparator is above a threshold voltage received by the comparator; and
storing counts of each counter of the one or more counters and generating a total photon count.

14. The method of claim 13, further comprising:
comparing the total photon count and a threshold count; and
generating a bandwidth control signal when the total photon count is less than the threshold count, the bandwidth control signal configured to couple an additional capacitor to a ground terminal, the additional capacitor is coupled to the CSA and the discriminator system, and wherein, the event detect signal is delayed by an additional delay to generate the convert signal, the additional delay is greater than the fixed delay.

15. The method of claim 14, further comprising:
receiving the total photon count in a first cycle; and
generating the bandwidth control signal on receiving a compare signal at an end of the first cycle and before beginning of a second cycle, the second cycle occurs after the first cycle.

16. The method of claim 14, wherein when the total photon count is less than the threshold count, a region of operation is in a low intensity region, and the bandwidth control signal activates a switch to couple the additional capacitor to the ground terminal.

17. The method of claim 12, further comprising generating a controlled voltage in a delay locked loop (DLL) in response to a clock signal, wherein the fixed delay is a function of the controlled voltage.

18. The method of claim 12, wherein resetting the CSA further comprises activating a secondary switch by the reset signal, the CSA includes a feedback capacitor, and the secondary switch is coupled in parallel to the feedback capacitor.

19. An imaging system comprising:
a gantry configured to receive a patient, the gantry is configured to rotate at a defined speed;
an x-ray source disposed in the gantry and configured to emit x-rays towards the patient; and
a plurality of detectors configured to receive to receive x-rays attenuated by the patient, at least one detector of the plurality of detectors configured to generate a current signal in response to the received attenuated x-rays, the at least one detector comprising:
a charge sensitive amplifier (CSA) configured to generate an integrated signal in response to the current signal;
an active comparator coupled to the CSA and configured to receive the integrated signal and a primary reference voltage signal, the active comparator configured to generate an event detect signal;
a first delay element coupled to the active comparator and configured to provide a fixed delay to the event detect signal to generate a convert signal; and
a discriminator system coupled to the CSA, wherein the discriminator system is configured to sample the integrated signal when activated by the convert signal.

20. The imaging system of claim 19, further comprising a reset switch coupled in parallel to the CSA, wherein the reset switch resets the CSA when activated by the convert signal.

* * * * *